(12) United States Patent
Tornier

(10) Patent No.: US 8,454,666 B2
(45) Date of Patent: Jun. 4, 2013

(54) SLIDE-TYPE ANTI-BACKOUT DEVICE FOR PROSTHESIS

(75) Inventor: Alain Tornier, Saint-Ismier (FR)

(73) Assignee: Clariance, Dainville (FR)

(*) Notice: Subject to any disclaimer, the term of this patent is extended or adjusted under 35 U.S.C. 154(b) by 318 days.

(21) Appl. No.: 12/843,162

(22) Filed: Jul. 26, 2010

(65) Prior Publication Data
US 2011/0029023 A1   Feb. 3, 2011

Related U.S. Application Data

(60) Provisional application No. 61/229,845, filed on Jul. 30, 2009.

(30) Foreign Application Priority Data

Jul. 30, 2009  (FR) ...................................... 09 03746

(51) Int. Cl.
*A61B 17/80* (2006.01)
(52) U.S. Cl.
USPC ............................................ 606/289; 606/71
(58) Field of Classification Search
USPC ................ 606/280–299, 70–71; 411/87, 102, 411/116, 125, 315–317
See application file for complete search history.

(56) References Cited

U.S. PATENT DOCUMENTS

| | | | | |
|---|---|---|---|---|
| 4,329,097 A * | 5/1982 | Steele et al. | ..................... | 411/88 |
| 5,876,402 A | 3/1999 | Errico et al. | | |
| 5,879,389 A | 3/1999 | Koshino | | |
| 6,602,255 B1 * | 8/2003 | Campbell et al. | ............. | 606/290 |
| 6,652,525 B1 * | 11/2003 | Assaker et al. | ................ | 606/296 |
| 6,945,973 B2 * | 9/2005 | Bray | ............................... | 606/287 |
| 7,468,069 B2 * | 12/2008 | Baynham et al. | ............. | 606/296 |
| 7,662,154 B2 * | 2/2010 | Ribeiro | ............................. | 606/70 |
| 7,887,547 B2 * | 2/2011 | Campbell et al. | ............. | 606/104 |
| 7,963,981 B2 * | 6/2011 | Binder et al. | ................. | 606/289 |
| 8,043,346 B2 * | 10/2011 | Markworth | .................... | 606/294 |
| 2005/0059971 A1 * | 3/2005 | Michelson | ....................... | 606/69 |
| 2006/0079901 A1 * | 4/2006 | Ryan et al. | ....................... | 606/69 |
| 2006/0195100 A1 | 8/2006 | Kirschman | | |
| 2006/0247639 A1 | 11/2006 | Anderson | | |
| 2007/0123884 A1 * | 5/2007 | Abdou | ............................ | 606/69 |
| 2008/0287999 A1 | 11/2008 | Markworth | | |
| 2009/0131988 A1 * | 5/2009 | Bush et al. | ..................... | 606/280 |
| 2010/0121383 A1 * | 5/2010 | Stanaford et al. | ............. | 606/280 |

FOREIGN PATENT DOCUMENTS

| | | |
|---|---|---|
| EP | 1500376 | 1/2005 |
| EP | 1 185 210 B1 | 4/2005 |
| WO | 2004039236 | 5/2004 |
| WO | 2005102192 | 11/2005 |

OTHER PUBLICATIONS

French Search Report dated Dec. 2, 2009 from French Application No. 0903746.

* cited by examiner

*Primary Examiner* — Todd Manahan
*Assistant Examiner* — Eric S Gibson
(74) *Attorney, Agent, or Firm* — Young & Thompson

(57) ABSTRACT

A slide-type cervical plate includes an anti-backout device (2) preventing the vertical movements of the bone anchor screws (3) and which consists of first vertical-blocking elements (71) capable of deforming elastically in a first direction so that an anchor screw (3) can be introduced into the corresponding bore (4) and of second vertical-blocking elements (8) capable of deforming elastically in a second direction different than the first so that another anchor screw (3) can be fitted into another bore (4), the first and second blocking elements deforming elastically when a combined external load in a vertical direction and in rotation in the clockwise direction is applied to the anchor screws (3).

8 Claims, 8 Drawing Sheets

SLIDE-TYPE ANTI-BACKOUT DEVICE FOR PROSTHESIS

BACKGROUND OF THE INVENTION

1. Field of the Invention

The present invention relates to a slide-type cervical plate and more particularly to an anti-backout device with which said cervical plate is equipped and which is intended to hold the bone anchor screws in position.

2. Description of the Related Art

U.S. Pat. No. 5,876,402 discloses a locking device comprising a screw and a plate which are intended to immobilize bones by fixation thereinto, notably into the vertebral bodies of a spinal column.

The plate has through-holes with a conically tapered profile into which are respectively introduced a fixation screw with a spherical head and a conical coupling element which fits around the screw head and presses against the conical edges of the hole.

Each through-hole in its upper part and above the conical coupling element has a coaxial slot intended to accept a locking element formed of a split annular clamp. The split clamp is centered about the axis of the conically profiled hole, preventing any backing-out of the conical coupling element.

U.S. Pat. No. 5,879,389 discloses a knee prosthesis the tibial plate of which is fixed into the bone using anchor screws housed in holes that pass through said plate. The upper bore of the hole that accommodates the head of each screw has a coaxial slot intended to accommodate a split annular clamp preventing screw backout.

Also, European patent EP 1 185 210 discloses an orthopedic implant comprising an anti-backout device comprising:

at least one housing which is axially offset with respect to the main axes XX' and YY' of the bore, and at least one retaining means which collaborates with the corresponding housing so that said retaining means partially crosses the corresponding bore accepting the fixator screw so as to be able to deform elastically under a pressing load so as to allow the screw to pass and be fitted into its bore, whereas the retaining means reverts to a non-deformed original position when the pressing load ceases to be applied, so that it comes into position over the head of the screw so as to prevent the latter from moving with respect to the implant in a direction parallel to the longitudinal axis of the bore.

BRIEF SUMMARY OF THE INVENTION

The slide-type cervical plate and the anti-backout device thereof are aimed at making it easier to fit the fixator screws and at guaranteeing that the latter are perfectly immobilized in terms of vertical translation with respect to said cervical plate.

The slide-type cervical plate according to the present invention comprises at least one anti-backout device collaborating with at least two bores positioned on one and the same axis AA' parallel to that XX' of said cervical plate, said anti-backout device preventing the vertical displacements along the axis ZZ' with respect to said cervical plate of bone anchor screws each positioned inside a bore provided with a shoulder against which the head of said screw presses when this screw is tightened, the anti-backout device consisting of first vertical-blocking means capable of deforming elastically in a first direction so that an anchor screw can be introduced into the corresponding bore and of second vertical-blocking means capable of deforming elastically in a second direction different than the first so that another anchor screw can be fitted into another bore, said first and second blocking means deforming elastically when a combined external load in a vertical direction along the axis ZZ' and in rotation in the clockwise direction is applied to the anchor screws (3).

The slide-type cervical plate according to the present invention comprises an anti-backout device which consists, in the thickness of said cervical plate, of a housing opening in a horizontal direction into each bore via a slot created above the corresponding shoulder, of a tab capable of deforming elastically between two bores in a first direction, and of a slide-forming platform positioned inside the housing so as to collaborate with the tab, said slide platform comprising, on the one hand, anti-backout stops passing through each slot to emerge inside the corresponding bore and, on the other hand, a slot delimiting a connecting bridge allowing the platform to deform elastically in a second direction different than the first.

The slide-type cervical plate comprising an anti-backout device according to the present invention comprises a tab which is able to deform elastically in a first direction on each side of an axis YY' when an external load is applied to the platform.

The slide-type cervical plate comprising an anti-backout device according to the present invention comprises a tab which at its free end comprises a slot so that said tab adopts a forked endshape.

The slide-type cervical plate comprising an anti-backout device according to the present invention comprises a housing which comprises, perpendicular to the tab, a pressing and sliding face.

The slide-type cervical plate comprising an anti-backout device according to the present invention comprises a slide platform which comprises, in its middle, a slot collaborating with the slot of the tab of the housing so that said platform is guided inside said housing.

The slide-type cervical plate comprising an anti-backout device according to the present invention comprises a slide platform which comprises, on each side of the slot, edges with a bulbous profile so that they form the anti-backout stops of the vertical-blocking means that emerge respectively inside each bore and above the shoulders.

The slide-type cervical plate comprising an anti-backout device according to the present invention comprises a slot which delimits a tab that presses against the sliding face of the housing and a connecting bridge able to deform elastically in a second direction different than the first when an external load is applied to the platform.

The slide-type anti-backout device that limits the vertical movements of the anchor screws housed in bores of a prosthesis according to the present invention consists of first vertical-blocking means able to deform elastically in a first direction so that an anchor screw can be introduced into the corresponding bore and of second vertical-blocking means able to deform elastically in a second direction different than the first so that another anchor screw can be fitted into another bore.

The slide-type anti-backout device according to the present invention consists, in the thickness of the prosthesis, of a housing opening in a horizontal direction inside each bore via a slot formed above a corresponding shoulder, of a tab able to deform elastically between two bores in a first direction, and of a slide-forming platform positioned inside the housing so as to collaborate with the tab, said slide platform comprising, on the one hand, anti-backout stops passing through each slot to emerge inside the corresponding bore and, on the other hand, a slot allowing the platform to deform elastically in a second direction different than the first.

The description which will follow, with reference to the attached drawings given by way of nonlimiting examples, will permit a better understanding of the invention, of the features it exhibits and of the advantages it is able to afford:

DETAILED DESCRIPTION OF THE PREFERRED EMBODIMENTS

Figure 1:
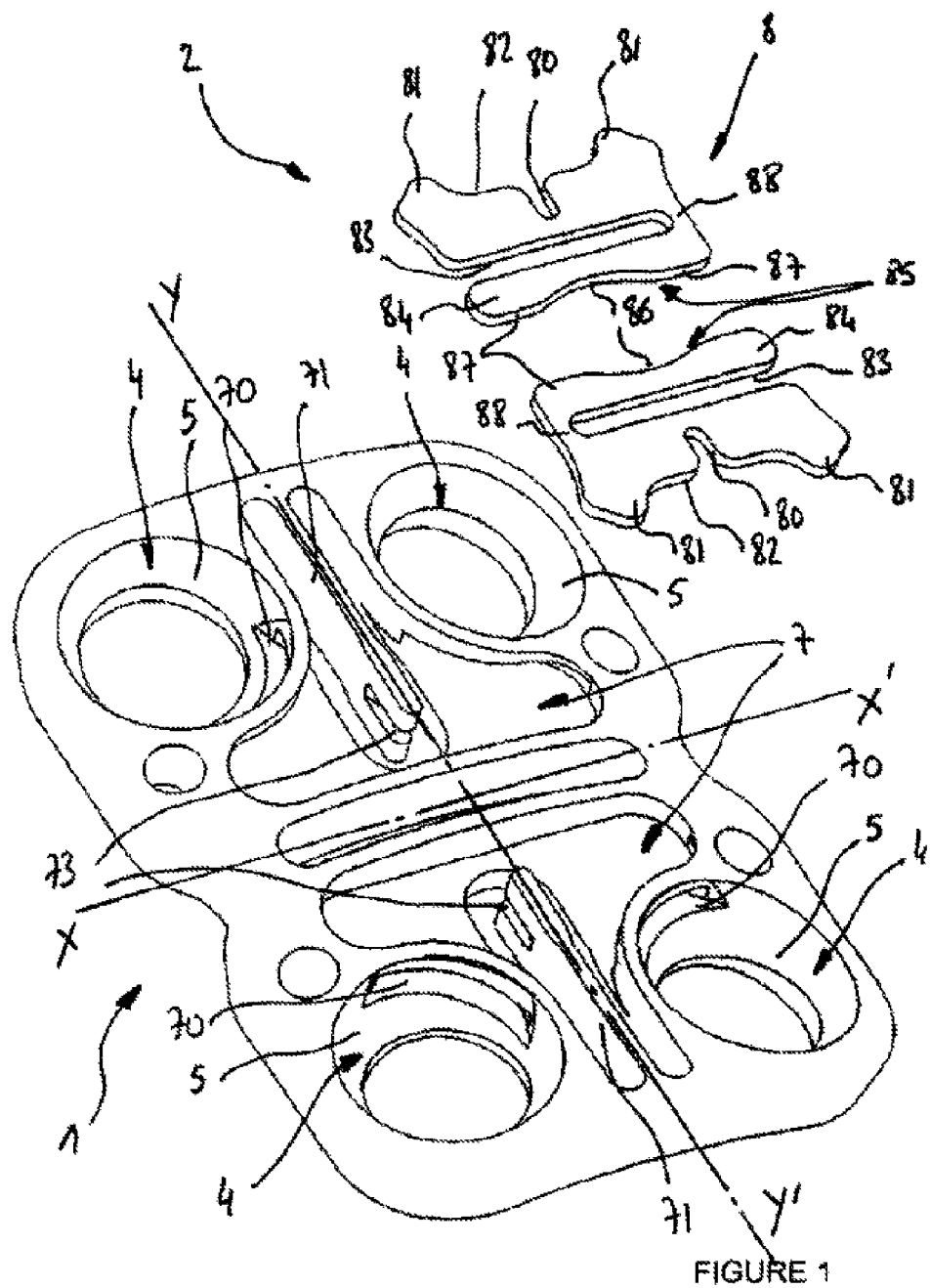
FIGS. 1 and 2 are perspective views illustrating a slide-type cervical plate comprising an anti-backout device intended to hold the bone anchor screws in position according to the present invention.
Figure 2:
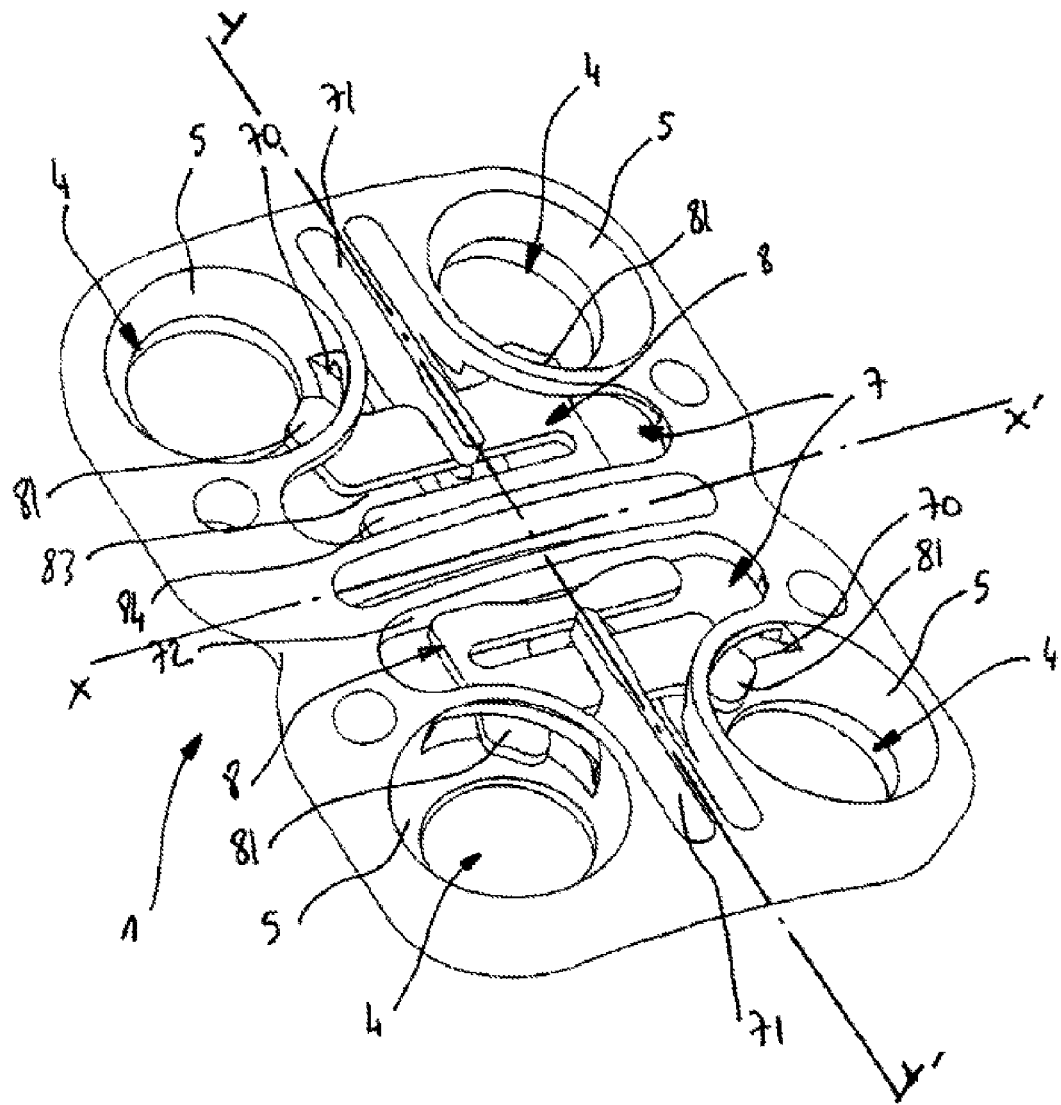

FIGS. 1 and 2 show a cervical plate 1 comprising at least one anti-backout device 2 that prevents the vertical movements of the bone anchor screws 3 with respect to said plate. It goes without saying that the fitting of an anti-backout device 2 according to the present invention for a cervical plate 1 is given by way of example.

The cervical plate 1 has, in a horizontal plane, a substantially rectangular profile defined by the main reference axes XX' and YY'.

The cervical plate 1 is pierced along a vertical axis ZZ' with through-bores 4 each provided with a shoulder 5 which, for example, has a profile in the form of a portion of a sphere. Each bore 4 collaborates with an anchor screw 3 comprising a head 6 the external profile of which complements that of the shoulder 5 so as to press against the latter when said screw is tightened and the cervical plate 1 is immobilized.

The bores 4 are positioned in pairs in a horizontal plane along a first axis AA' parallel to the axis XX' of the cervical plate 1 and along a second axis BB' parallel to the axis YY' of said plate.

The anti-backout device 2 consists, in the thickness of the cervical plate 1 and between two bores 4 positioned along the same horizontal axis AA', of a housing 7 that is centered with respect to the axis YY' of said plate and which opens in a horizontal direction perpendicular to the axis ZZ' into each bore 4 via a slot 70 formed above the corresponding shoulder 5.

The anti-backout device 2 comprises first vertical-blocking means which are able to deform elastically in a first direction with respect to the axis YY' of the cervical plate 1.

For that, the housing 7 has a substantially T-shaped profile comprising, between the corresponding two bores 4 borne by the axis YY' of the cervical plate 1, a tab 71 capable of deforming elastically on each side of said axis YY'. The tab 71 at its free end comprises a slot 73 so that said tab has a forked end. The housing 7 comprises, perpendicular to the tab 71 and in the vicinity of the main axis XX' of the cervical plate 1, a pressing and sliding face 72.

The anti-backout device 2 comprises a reversible platform 8 of substantially rectangular shape constituting a slide which is positioned inside the housing 7 in the same horizontal plane as the cervical plate 1 so that it can move inside said housing and constitute the means of vertically blocking the anchor screws 3 in the corresponding bores 4.

The movement of the platform 8 inside the housing 7 is controlled by the elastic deformation of the tab 71 so that said platform slides along the pressing face 72.

For that, the platform or slide 8 has in its middle a slot 80 that collaborates with the slot 73 of the tab 71 of the housing 7 so that said platform is guided inside said housing.

The platform or slide 8 comprises, on each side of the slot 80, edges 81 with a bulbous profile delimiting, above said slot, an empty space 82 so that only the edges 81 pass through the corresponding slot 70. The free ends of the bulbous edges 81 emerge respectively inside each bore 4 and above the shoulders 5 so as to constitute an anti-backout stop of the vertical-blocking means.

The anti-backout device 2 comprises second vertical blocking means which are able to deform elastically. For that, the platform or slide 8 comprises, in a direction perpendicular to that of the slot 80, another slot 83 of larger dimensions than the first so as to give said platform a certain elasticity.

The slot 83 delimits, opposite the bulbous edges 81 and in a direction perpendicular to the slot 80, a tab 84 and a connecting bridge 88 which is able to deform elastically under external load.

The tab 84 comprises on its external edge 85 and in its middle a hollow 86 delineating at each end two flat faces 87 forming contact regions that come to press against the sliding face 72 of the housing 7.

The platform or slide 8 is introduced into the housing 7 by deforming its connecting bridge 88 so that the slot 80 penetrates the slot 73 formed at the free end of the tab 71 and so that its bulbous edges 81 emerge inside each bore 4 of the cervical plate 1.

The platform or slide 8 is left free to move inside the housing 7 because the distance between the end of the slot 73 of the tab 71 and the sliding face 72 is shorter than the distance between the end of the slot 80 of the platform 8 and the flat face 87 of the external edge 85.

The tab 71 of the housing 7 delineates the axis of pivoting and of movement or sliding of the platform 8 inside said housing 7.

First Elastically Deformable Blocking Means of the Anti-Backout Device 2

Figure 3:
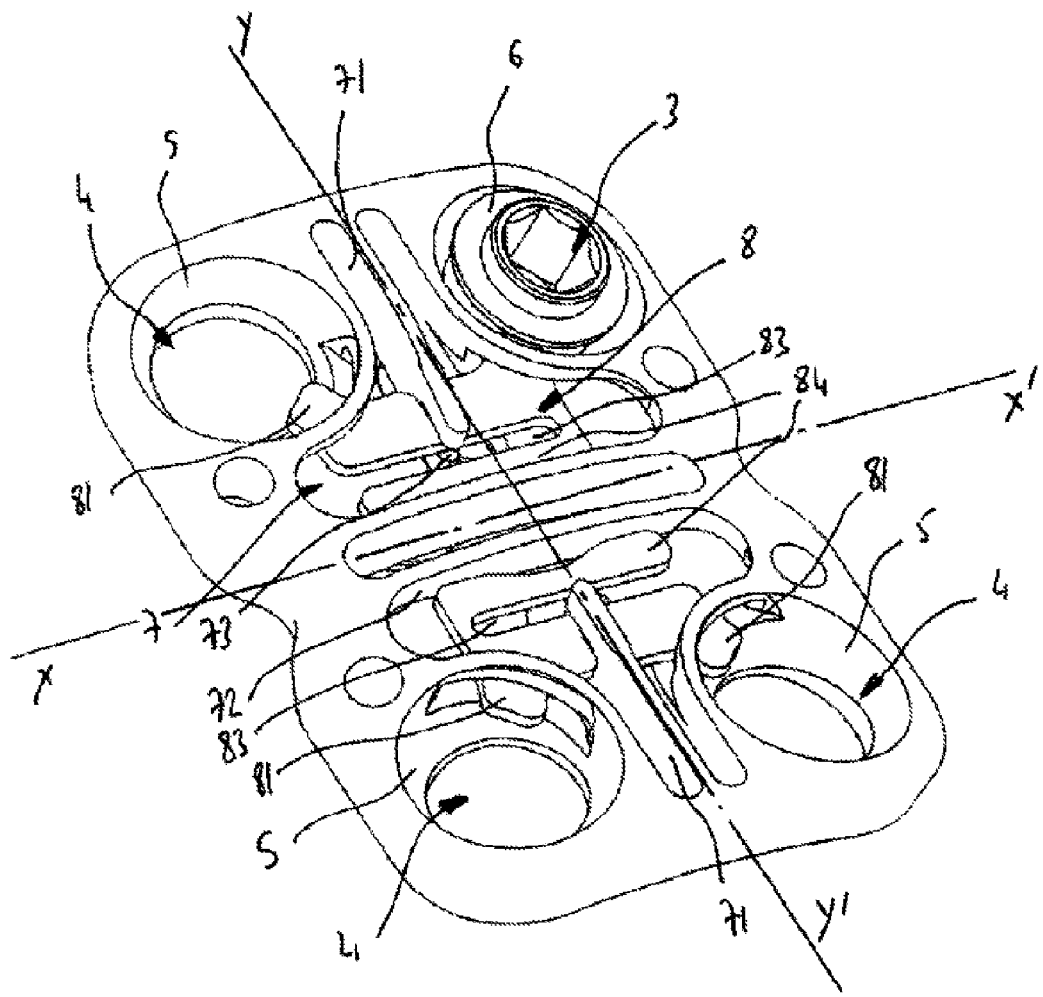
FIGS. 3 and 4 are views illustrating the fitting of the bone anchor screws into the bores of the slide-type cervical plate provided with the anti-backout device equipped with its first blocking means able to deform elastically in a first direction.
Figure 4:
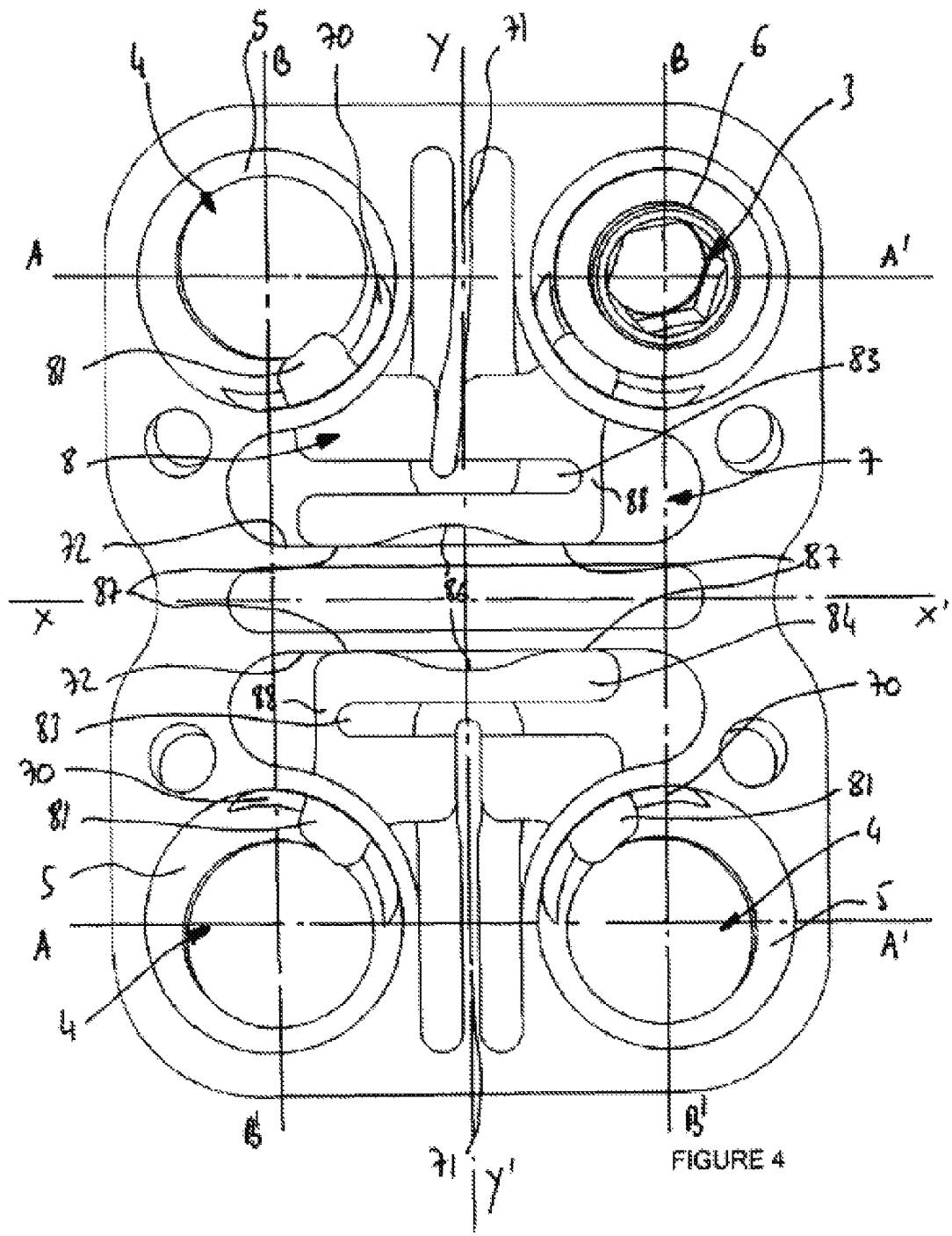

Thus, when the first anchor screw 3 is fitted into its bore 4 and, for example, the one toward the end of the slot 83 of the platform 8, it will be noted that the head 6 of said screw makes it possible, under the external vertical load of insertion and a combined load of turning in a clockwise direction, for the first blocking means consisting of the corresponding bulbous edge 81 of said platform 8 to be pushed toward the outside of said bore, causing deformation of the tab 71 as a consequence of the sliding of the flat faces 87 of the edge 85 along the face 72 of the housing 7 to allow the head 6 to pass freely until this head comes to press against the shoulder 5 (FIGS. 3 and 4).

After the head 6 of the anchor screw 3 has passed, the tab 71 because of its elasticity reverts to its original position returning the platform 8 in a sliding movement in the opposite direction until its bulbous edge 81 emerges inside the bore 4 above said head 6, to block any vertical movement of the anchor screw 3 (FIGS. 3 and 4).

Second Elastically Deformable Blocking Means of the Anti-Backout Device 2

Figure 5:
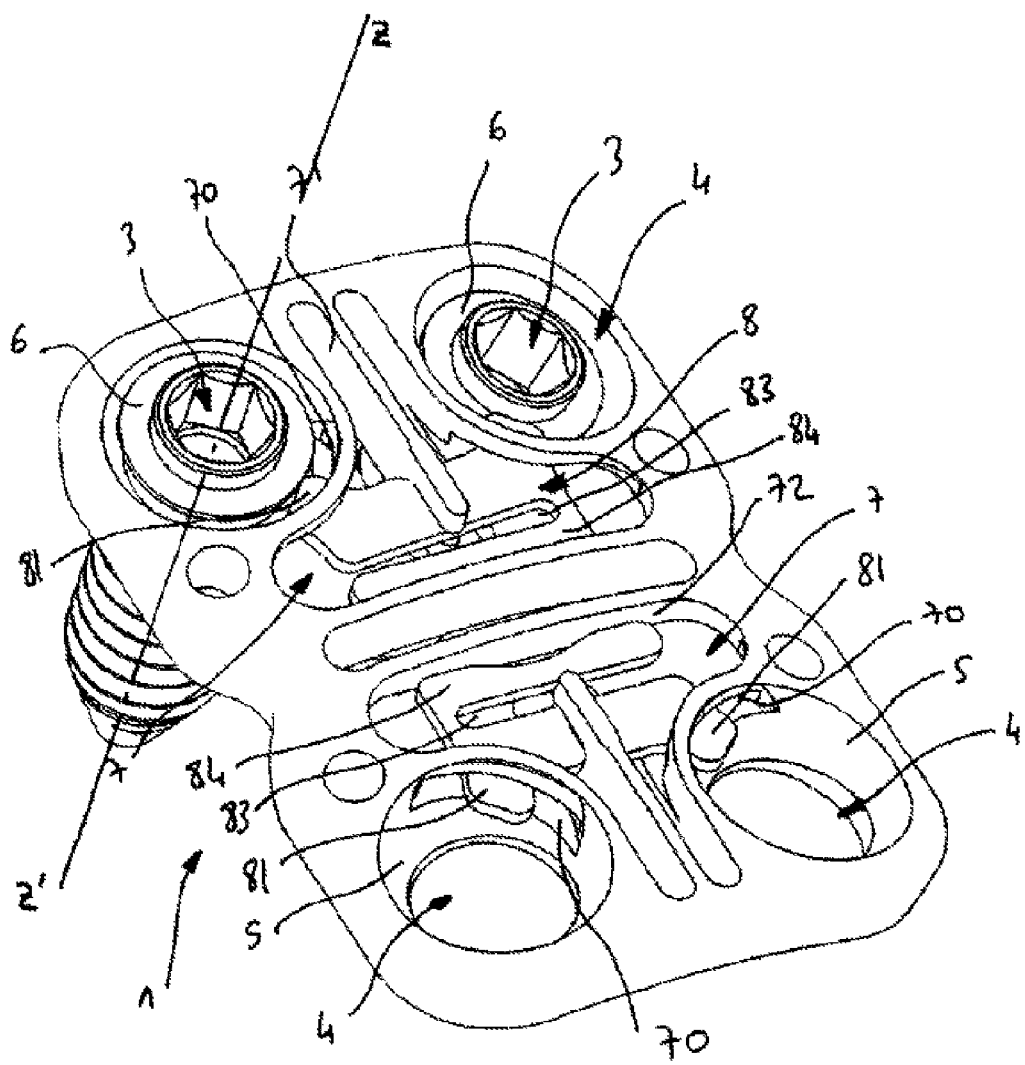
FIGS. 5 and 6 are views illustrating the fitting of the bone anchor screws into the bores of the slide-type cervical plate provided with the anti-backout device equipped with its second blocking means able to deform elastically in a second direction different than the first.
Figure 6:
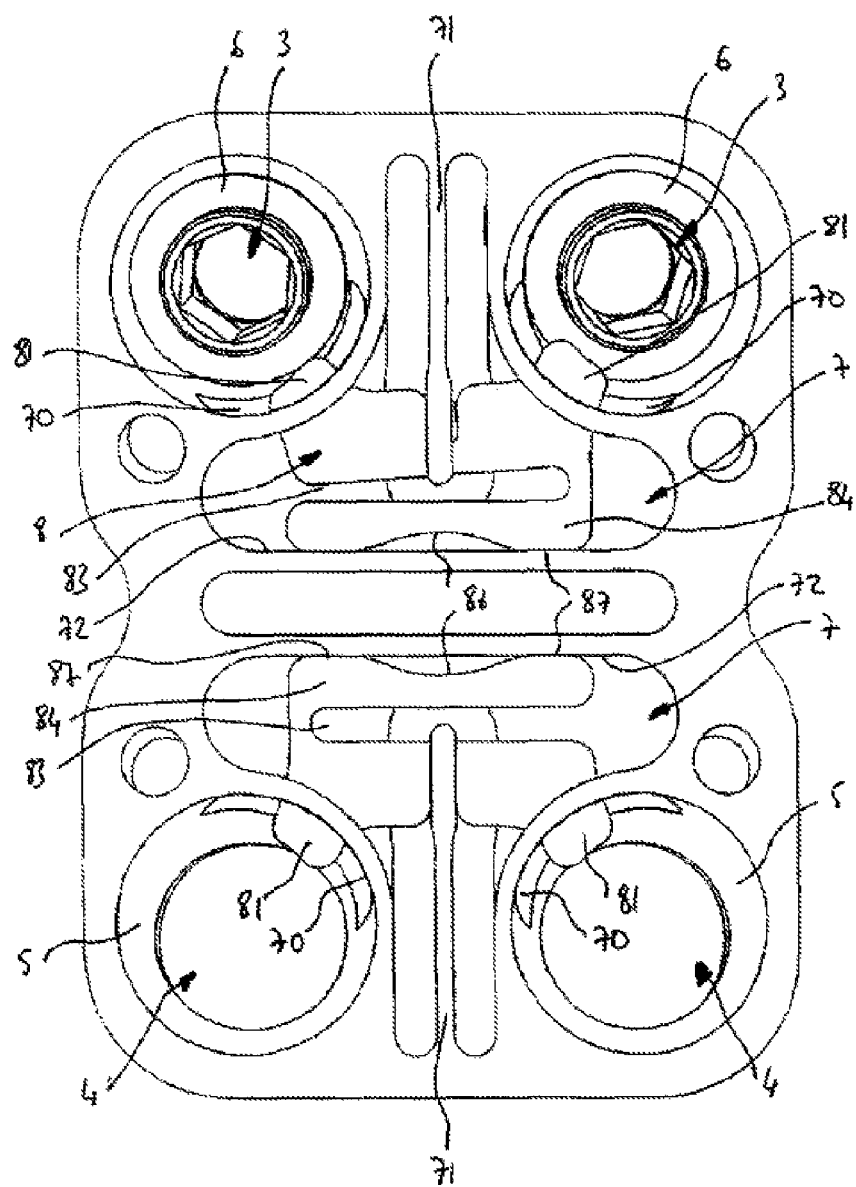

The second anchor screw 3 is fitted inside the bore 4, for example on the side of the open part of the slot 83 of the platform, by elastic deformation of the connecting bridge 88 (FIGS. 5 and 6).

It will be noted that the head 6 of the other anchor screw 3 makes it possible, under an external vertical load of insertion and a combined load of turning in the clockwise direction, for the second blocking means consisting of the other bulbous edge 81 of the platform 8 to be pushed toward the outside of the bore 4 because of the deformation of the body of said platform and of the connecting bridge 88 so as to allow the head 6 to pass freely until this head has come to press against the shoulder 5.

After the head 6 of the anchor screw 3 has passed, the body of the platform 8 and, more specifically, the connecting bridge 88, reverts as a result of its elasticity to its original position, allowing the corresponding bulbous edge 81 to move inside the bore 4 and above said head 6 to block any vertical movement of the anchor screw 3 (FIGS. 5 and 6).

Figure 7:
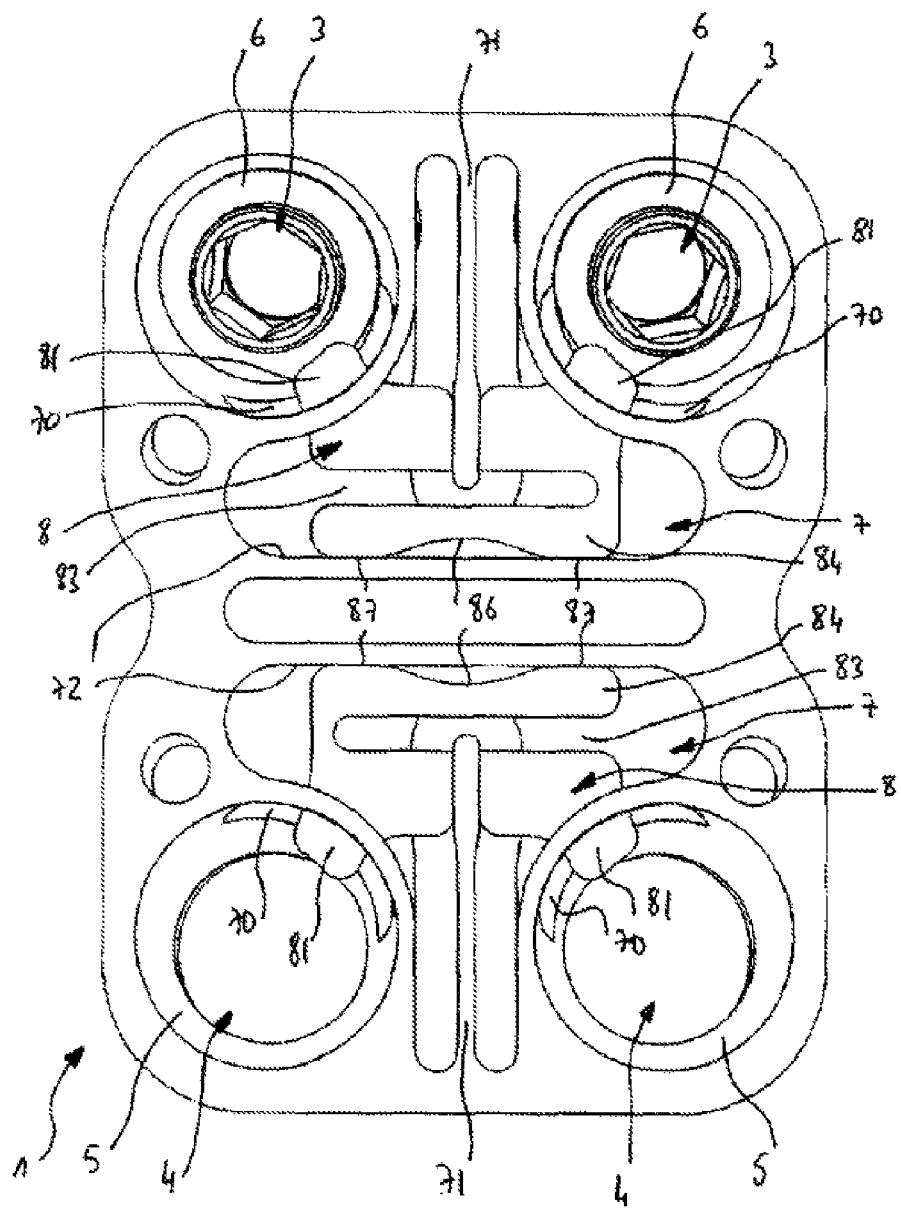
FIGS. 7 and 8 are views showing the cervical plate the bone anchor screws of which are held vertically in position with respect to said plate by the anti-backout device according to the present invention.
Figure 8:
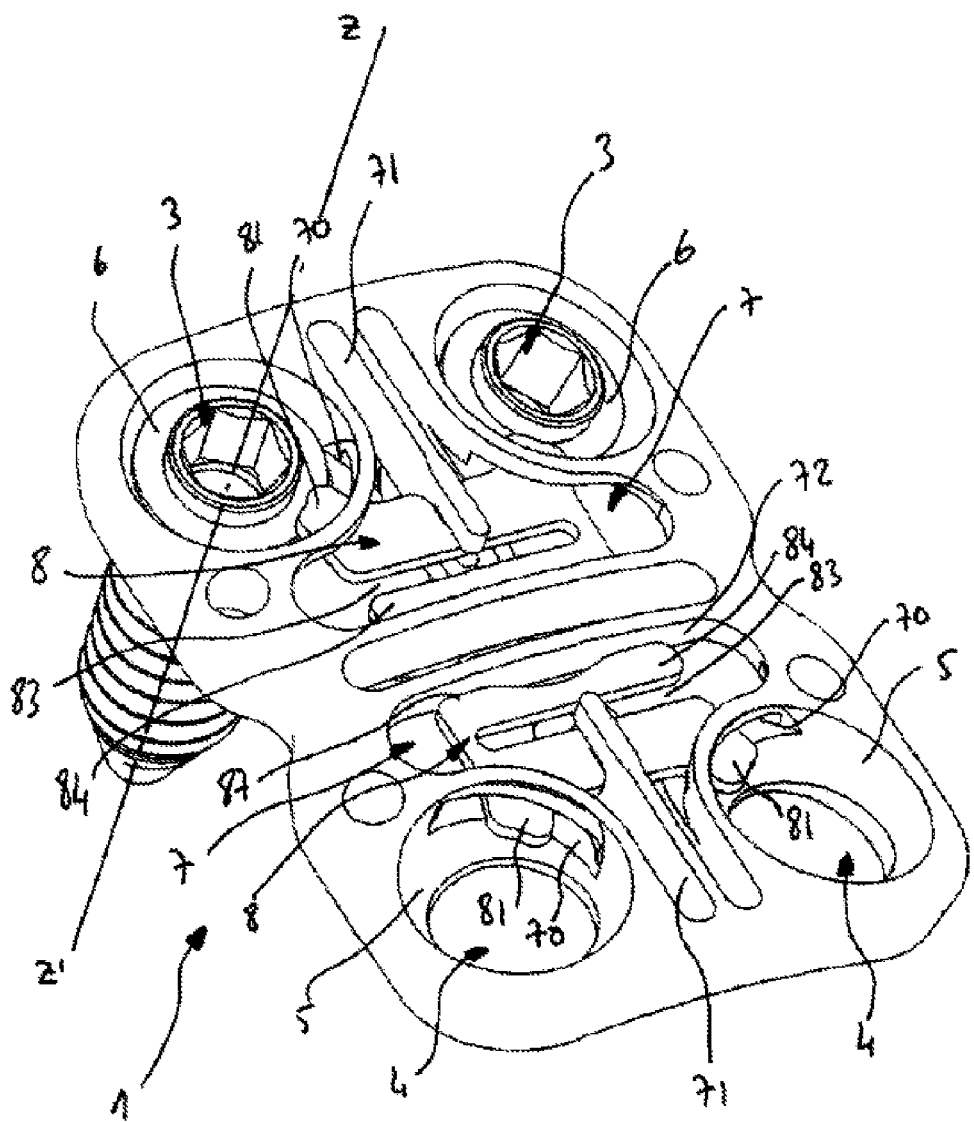

Specifically, each bulbous edge 81 of the platform 8 constitutes, inside the corresponding bore 4, a stop that prevents the removal or backing-out of the anchor screw 3 from said bore 4 (FIGS. 7 and 8).

The same is true of the other anchor screws 3 of the cervical plate 1 according to the present invention by symmetry along the axis XX' of said plate.

The anti-backout device 2 according to the present invention can be arranged on any type of cervical plate or any other prosthesis or implant attached using anchor screws, the latter being held in position with respect to the prosthesis, the implant or the plate.

It must also be understood that the foregoing description has been given merely by way of example and that it does not in any way restrict the field of the invention the described embodiment details of which could be replaced by any other equivalents without departing from the field of the invention.

The invention claimed is:

1. A slideable cervical plate comprising:
   at least one anti-backout device (2) collaborating with at least two bores (4) positioned on one and the same axis AA' parallel to that XX' of said cervical plate (1), said anti-backout device (2) preventing the vertical displacements along the axis ZZ' with respect to said cervical plate (1) of bone anchor screws (3) each positioned inside a bore (4) provided with a shoulder (5) against which the head (6) of said screw (3) presses when the screw (3) is tightened,
   wherein the anti-backout device (2) comprises:
      first means for vertical-blocking capable of deforming elastically in a first direction so that an anchor screw (3) can be introduced into the corresponding bore (4), and
      second means for vertical-blocking capable of deforming elastically in a second direction different than the first so that another anchor screw (3) can be fitted into another bore (4), said first and second means for blocking deforming elastically when a combined external load in a vertical direction along the axis ZZ' and in rotation in the clockwise direction is applied to the anchor screws (3);
      in the thickness of said cervical plate (1), a housing (7) opening in a horizontal direction into each bore (4) via a slot (70) created above the corresponding shoulder (5),
      a tab (71) capable of deforming elastically between two bores (4) in the first direction, and
      a slide-forming platform (8) positioned inside the housing (7) so as to collaborate with the tab (71),
   wherein said slide platform (8) comprises:
      anti-backout stops (81) passing through each slot (70) to emerge inside the corresponding bore (4),
      a slot (83) delimiting a connecting bridge (88) allowing the platform (8) to deform elastically in the second direction different than the first, and
      in a middle of the slide platform (8), a slot (80) collaborating with the slot (73) of the tab (71) of the housing (7) so that said platform is guided inside said housing.

2. The slideable cervical plate comprising an anti-backout device according to claim 1, wherein the tab (71) is able to deform elastically in a first direction on each side of an axis YY' when an external load is applied to the platform (8).

3. The slideable cervical plate comprising an anti-backout device according to claim 1, wherein the tab (71) at a free end comprises a slot (73) so that said tab adopts a forked end-shape.

4. The slideable cervical plate comprising an anti-backout device according to claim 1, wherein the housing (7) comprises, perpendicular to the tab (71), a pressing and sliding face (72).

5. The slideable cervical plate comprising an anti-backout device according to claim 4, wherein the slot (83) delimits a tab (84) that presses against the sliding face (72) of the housing (7) and a connecting bridge (88) able to deform elastically in a second direction different than the first when an external load is applied to the platform (8).

6. The slideable cervical plate comprising an anti-backout device according to claim 1, wherein the slide platform (8) comprises, on each side of the slot (80), edges (81) with a bulbous profile so that they form the anti-backout stops of the means for vertical-blocking that emerge respectively inside each bore (4) and above the shoulders (5).

7. The slideable cervical plate comprising an anti-backout device according to claim 1, wherein the slot (83) delimits a tab (84) that presses against the sliding face (72) of the housing (7) and a connecting bridge (88) able to deform elastically in a second direction different than the first when an external load is applied to the platform (8).

8. The slideable cervical plate comprising an anti-backout device according to claim 1,
   wherein the first direction is perpendicular to the second direction.

* * * * *